United States Patent [19]

Drauz et al.

[11] Patent Number: 4,628,126

[45] Date of Patent: * Dec. 9, 1986

[54] PROCESS FOR THE PRODUCTION OF DIHYDROXYBENZENES

[75] Inventors: Karlheinz Drauz, Freigericht; Axel Kleemann, Hanau, both of Fed. Rep. of Germany

[73] Assignee: Degussa Aktiengesellschaft, Frankfurt, Fed. Rep. of Germany

[*] Notice: The portion of the term of this patent subsequent to May 20, 2003 has been disclaimed.

[21] Appl. No.: 588,847

[22] Filed: Mar. 12, 1984

[30] Foreign Application Priority Data

Mar. 11, 1983 [DE] Fed. Rep. of Germany ....... 3308726

[51] Int. Cl.$^4$ ............................................. C07C 37/00
[52] U.S. Cl. .................................. 568/771; 568/741; 568/803
[58] Field of Search ............... 568/803, 771, 768, 798, 568/800, 741

[56] References Cited

U.S. PATENT DOCUMENTS 3,943,179  3/1976  Bost ..................................... 568/771

FOREIGN PATENT DOCUMENTS

| | | |
|---|---|---|
| 2162589 | 7/1972 | Fed. Rep. of Germany . |
| 2138735 | 3/1973 | Fed. Rep. of Germany ...... 568/771 |
| 1543830 | 6/1973 | Fed. Rep. of Germany ...... 568/771 |
| 2341743 | 2/1974 | Fed. Rep. of Germany ...... 568/771 |
| 2304602 | 8/1974 | Fed. Rep. of Germany . |
| 2407398 | 12/1977 | Fed. Rep. of Germany . |
| 2064497 | 8/1978 | Fed. Rep. of Germany ...... 568/771 |
| 2341743 | 2/1981 | Fed. Rep. of Germany ...... 568/771 |
| 2462957 | 6/1981 | Fed. Rep. of Germany . |
| 7312990 | 4/1974 | Netherlands ...................... 568/771 |

OTHER PUBLICATIONS

Ullmanns Encyklopadie der Technischen Chemie 4., Neubearbeitete und Erweiterte Auflage–Band 17–Milchsaure bis Petrolkoks.

*Primary Examiner*—Werren B. Lone
*Attorney, Agent, or Firm*—Cushman, Darby & Cushman

[57] ABSTRACT

The nuclear hydroxylation of phenol with organic solutions of hydrogen peroxide in the presence of a catalyst is carried out in improved manner by employing both (1) a special, practically water free solution of hydrogen peroxide in an organic solvent which does not form an azeotrope with water or whose highest azeotrope with water, boil near or above the boiling point of hydrogen peroxide, and (2) employing as a catalyst $XO_2$ where X is sulfur, selenium, or tellurium. Besides increasing the yield and the ability to carry out the reaction in a simpler manner when selenium dioxide is employed as a catalyst, there can also be controlled the ortho-para ratio, respectively, the ortho-ortho ratio of the product.

43 Claims, No Drawings

PROCESS FOR THE PRODUCTION OF DIHYDROXYBENZENES

BACKGROUND OF THE INVENTION

The invention is directed to the production of dihydroxybenzenes as well as their monoethers by nuclear hydroxylation of the corresponding phenols or phenyl ethers with hydrogen peroxide.

Important dihydroxybenzenes are derivatives of phenol, the napthols, and also derivatives of anthracene and phenanthrene. They are employed in the production of dyestuffs, in the production of synthetic resins, in photography, and for the production of important plant protectives. Thus, e.g., hydroquinone, the para hydroxylation product of phenol is used as a photo chemical; pyrocatechol, the corresponding ortho product for plant protection. For various areas of use, such as, e.g., as antioxidants, the dihydroxyphenols are mutually useful.

Their production, therefore, has long been the object of thorough investigations. The hydroxylation has been carried out both with hydrogen peroxide itself as well as with hydroperoxides, peroxides, or even per acids such as, e.g., performic acid or peracetic acid.

Nevertheless, hydrogen peroxide was preferred since it is the most readily available and since with percarboxylic acids, hydroperoxides and peroxides side reactions occur (European published application 0027593).

There was always present a catalyst in these hydroxylations. This catalyst can be a metalloid such as sulfur, selenium, tellurium, phosphorus, arsenic, or antimony in elemental form (German OS 2348957) or there can be used boron compounds (German Pat. No. 1543830).

Various processes operate with transition elements in the form of their ions (German OS 2162552), especially with iron ions (German OS 2162589 or German Pat. No. 2407398) or cobalt ions (German AS 2341743), or even with the corresponding oxides (Milas U.S. Pat. No. 2,395,638).

Besides, there are employed strong acids such as sulfuric acid, sulfonic acids (German OS 2138735, German AS 2410742, German AS 2410758, German AS 2462967), or a mixture of sulfuric acid and phosphoric acid (German OS 2138735), there are also mentioned in the last named published application organic acids such as, inter alia, trichloroacetic acid or tartaric acid.

The already mentioned percarboxylic acids likewise serve as catalysts (French Pat. No. 1479354). In all of the mentioned catalysts, it is a matter with the catalysts being solid or liquid materials. Hydrogen peroxide, as preferred oxidation agent, for the most part is employed in aqueous solutions of various concentrations up to very high concentrations which have the danger of explosion; thus, the process according to German Pat. No. 2064497 operates with solutions which only contain 5 weight % water, but even at this highly concentrated hydrogen peroxide the yield of dihydroxy derivatives was only 70% and was reduced considerably correspondent to the dilution of the hydrogen peroxide.

Additionally, in these and also in other processes, the operation must be carried out with a very large excess of the phenol to be hydroxylated in order in general to obtain the above-stated yield. If this excess is reduced, e.g., from 20 moles to 10 moles per mole of hydrogen peroxide, then the yield is reduced drastically despite the higher concentration of hydrogen peroxide.

However, as is known, this type of excess of a reactant, which must be recycled, requires additional industrial expense; above all in regard to the size of the apparatus employed.

Since care is always taken to avoid large excesses of one component as far as possible, there have been attempts to avoid employing aqueous solutions of hydrogen peroxide.

Thus, different solutions of hydrogen peroxide in organic solvents have already been used. For example, according to the process of German Pat. No. 2410758, there are preferably employed hydrogen peroxide solutions in derivatives of phosphoric acid or phosphonic acid, namely in the presence of a strong acid, such as sulfuric acid (100%) or fluorosulfonic acid.

However, these highly concentrated strong acids have the disadvantage that their separation from the reaction mixture creates difficulties (German AS 2658943), above all since their concentration in the reaction mixture has a considerable influence on the length of the reaction.

The excess of phenol was indeed reduced somewhat in contrast to this in the process of German AS 2064497, but this did not outweigh the disadvantage of the strong acids.

An additional difficulty in the process of German Pat. No. 2410758 in the working up of the reaction mixture was produced by the presence of the water formed after the reaction with hydrogen peroxide.

Since the solvent for hydrogen peroxide employed in part is higher boiling than the phenol employed and this, especially with phenol itself, forms an azeotrope with water whose boiling point is below that of the organic solvent, it was highly problematic that a trouble-free separation of the excess phenols from the reaction mixture could be attained.

Therefore, other ways were tried, first to manage without catalyst, i.e., above all without the strong acids. Since the catalysts above all were needed for the activation of hydrogen peroxide, the process of German AS 2658823 was operated with organic solutions of peracetic acid. An additional catalyst was not used.

Entirely apart from the fact that the mentioned process presupposes a complete plant for the production of an organic percarboxylic acid, which first is obtained from hydrogen peroxide and carboxylic acid, and thereupon is produced by extraction of this so-called "equilibrium acid" from its aqueous solution, it has been shown a stated good selectivity and good yield was only possible in the presence of additional peracid stabilizers (German OS 2364181; European OS 0027593).

Using the same hydroxylation agent, but at different reaction temperatures, there occurs practically no change in the selectivity, see Table 1 of German Pat. No. 2364181.

Also, the addition of specific, chelate complex forming materials does not produce a remedy (German Pat. No. 2364181).

Likewise, changes of the reaction time have no influence on the selectivity (European OS 0027593).

From what has been said above, there is no known process either in the use of hydrogen peroxide itself or in the form of its per compounds, especially its percarboxylic acids, in spite of various additives as catalysts or stabilizers, which makes possible in a specific system on the one hand satisfactory yields and on the other hand also a regulation of the ratio of ortho to para compounds or of ortho compounds to each other, as they occur in the substituted phenols obtained in the hydroxylation. In a given system, whose essential parameters were the particular hydroxylation agent and the particular catalyst, respectively, the particular catalysts, the selectivity represents a specific factor.

Since the ortho and para compounds or the ortho compound together as isomers are not identical in their properties and, therefore, indeed in part find different industrial uses, it became desirable to be able to influence the selectivity in the production of these two isomrs without great industrial expense, i.e., above all in a still further shifting of the equilibrium in favor of one of the two isomers, especially, e.g., of pyrocatechol, or e.g., of 4-methyl-pyrocatechol. Thereby, it is essential that the predetermined parameters of a system must not be changed.

The purpose of the invention, therefore, is to carry out the nuclear hydroxylation of phenol and substituted phenols or their ethers with hydrogen peroxide in the presence of a catalyst in an industrially simpler manner and with very good yields.

SUMMARY OF THE INVENTION

It has now been found that this problem can be solved by employing an organic solution of hydrogen peroxide if the reaction is carried out in the presence of a catalyst of the formula $XO_2$ where X is sulfur, selenium, or tellurium and with a solution of hydrogen peroxide which has at most 1 wt. % of water and which preferably has a water content below 0.5 weight %, e.g., 0%, and which is produced with an organic solvent which does not form an azetrope with water or forms an azeotrope with water, which azeotrope has a boiling point near or above the boiling point of hydrogen peroxide, referred to normal pressure.

As catalysts, there are especially suited sulfur dioxide and selenium dioxide.

Sulfur dioxide can be employed both in the gaseous condition and in any desired solvent. This solvent should not enter into any disturbing reactions with hydrogen peroxide or sulfur dioxide.

Thus, there can be employed dialkyl ethers, e.g., diisopropyl ether, methyl tert. butyl ether, diisopropyl ether, diethyl ether, esters of phosphoric acid or phosphonic acid, e.g., trioctyl phosphate, tributyl phosphate, diethyl methanephosphonate, dibutyl ethane phosphonate, alkyl or cycloalkyl esters of saturated aliphatic carboxylic acids which contain 4–8 carbon atoms, e.g., alkyl alkanoates.

Especially suitable esters are those of acetic acid and propionic acid, above all n-propyl acetate or isopropyl acetate.

Other suitable esters include ethyl acetate, hexyl acetate, butyl acetate, sec. butyl acetate, amyl acetate, cyclohexyl acetate, cyclopentyl acetate, methyl propionate, ethyl propionate, propyl propionate, isopropyl propionate, butyl propionate, methyl butyrate, ethyl butyrate, n-propyl butyrate, ethyl valerate, ethyl hexanoate.

The concentration depends on the solubility of $SO_2$ in the solvent. Generally, it is between 0.1 and 50, preferably 1 to 10 weight %. However, it is favorable to employ sulfur dioxide as a solution in one of the above described carboxylic acid esters. Sulfur dioxide is used in very small amounts, i.e., in amount of 0.0001 to 0.1 mole, preferably from 0.0005 to 0.01 mole based on 1 mole of hydrogen peroxide, above all compared with hydroxylations catalyzed by protonic acids on the acid side.

The reaction generally occurs at 20° to 200° C., preferably at a temperature of 40° to 180° C.

The phenols employed for the nuclear hydroxylation are, in addition to phenol itself, substituted phenols as well as of phenol monoethers. Thus, there can be hydroxylated alkyl derivatives of phenol, e.g., where the alkyl group has 1 to 8 or 1 to 4 carbon atoms, e.g., the cresols, e.g., m-cresol, p-cresol or o-cresol, ethyl phenol, e.g., 2-ethyl phenol or 4-ethyl phenol, butyl phenols, e.g., 4-t-butylphenol or 4-n-butylphenol, 4-isopropyl phenol, 4-t-octylphenol, 4-n-octylphenol, the xylenols, e.g., 2,4-dimethyl phenol, the naphthols, e.g., 1-naphthol or 2-naphthol, 9-hydroxyanthracene, 9-hydroxyphenanthrene, as well as alkoxy compounds such as anisole, phenyl ethyl ether, phenyl butyl ether, phenyl isopropyl ether or p-cresol methyl ether, the alkyl or halogen derivatives of the alkoxy compounds, e.g., p-tolyl ethyl ether, p-tolyl methyl ether, methyl 4-chlorophenyl ether, also aryl phenols, such as 4-hydroxybiphenyl.

There can also be used halogen substituted phenols or alkoxy substituted phenols, e.g., 4-chlorophenol, 4-bromophenol, 4-fluorophenol, 3-chlorophenol, 2,4-dichlorophenol, 2-methoxyphenol, 4-ethoxyphenol.

Sulfur dioxide as a catalyst has no significant influence on the ratio of ortho to para compounds, respectively of ortho compounds to each other, as they are obtained in the hydroxylated phenols.

It has now been discovered that the above-mentioned ratio can be influenced by employing selenium dioxide as catalyst. Selenium dioxide is used in solid form, preferably in powder form, in an amount of 0.0001 to 0.5 mole, preferably from 0.0005 to 0.2 mole, based on 1 mole of hydrogen peroxide. It can also be used dissolved in solution. The reaction temperature is between 40° and 200° C., preferably between 40° and 170° C.

The pressure is not critical for the reaction. Generally, the reaction is carried out at normal pressure. A slight superatmospheric pressure up to about 2 bar is not unfavorable.

The use of selenium dioxide as catalyst makes it possible to control the ortho to para compound, respectively the ratios of two ortho compounds to each other, namely using one and the same reaction system. This was completely unexpected. For example, the theoretical ratio of ortho to para product in the hydroxylation of phenol is at about 2:1. The ratio obtained according to the state of the art now is generally between the values of nearly 1:1 to about 3.5:1, and it must be emphasized that the breadth of deviation of one of the mentioned values in a specific system was very small and could not be pushed as desired in favor of one or the other of the isomers.

Through the process of the invention, it is now possible to obtain ratios of ortho to para product of approximately 5:1 to 1:1.

If the para position to the OH group is occupied by a substituent, as for example a methyl group, then the new hydroxyl group can enter the molecule at one time ortho to the OH-group, on the other hand to the $CH_3$ group. The resulting products then are pyrocatechol or resorcinol substituted in the 4-position.

It is possible through the process of the invention to produce ratios of the two ortho hydroxylation products from about 5:1 to over 80:1.

This type of regulation of the two isomeric structures was not known previously. While selenium dioxide, as stated, is preferably employed in powdered form with sulfur dioxide in addition to the gaseous form, it has proven very suitable especially to employ freshly prepared solutions.

The hydrogen peroxide solutions in high boiling solvents whose water content at most is 1 weight %, preferably 0.5 weight % used according to the invention are produced according to the process of German patent application No. P.3308740.7 (and related Drauz U.S. application Ser. No. 510,162 filed July 1, 1983, the entire disclosure of which is hereby incorporated by reference and relied upon).

It is a matter of a solvent which either does not form an azeotrope with water or only forms an azeotrope with water which boils near or above the boiling point of hydrogen peroxide.

Among these solvents are phosphorus compounds of the formula

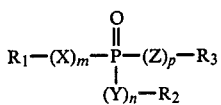

wherein X, Y, and Z stand for an O-atom or a N-($C_1$-$C_8$)-alkyl group or for a N-($C_4$-$C_7$)-cycloalkyl group, n, m, and p are each 0 or 1, $R_1$, $R_2$, and $R_3$ are straight or branched $C_1$-$C_8$ alkyl or $C_4$-$C_6$ cycloalkyl groups which in a given case can be substituted by halogen (e.g., chlorine, bromine, or fluorine), hydroxyl, $C_1$-$C_4$-alkoxy, —CN, or phenyl groups. Typical examples of such groups and compounds containing such groups are set forth in German Pat. No. 2038319 on col. 3, line 50, to col. 4, line 63, and col. 8, line 58, to col. 13, line 58. The entire disclosure of German Pat. No. 2038319 is incorporated by reference.

Above all, there are suited trialkyl phosphates having $C_1$-$C_8$-alkyl groups for the production of organic solutions of hydrogen peroxide according to the invention. Illustrative of such phosphates are trimethyl phosphate, triethyl phosphate, methyl diethyl phosphate, tributyl phosphate, tripropyl phosphate, triisopropyl phosphate, triisobutyl phosphate, tri sec. butyl phosphate, triamyl phosphate, trihexyl phosphate, trioctyl phosphate, tri 2-ethylhexyl phosphate. The preferred phosphate are triethyl phosphate and tributyl phosphate.

Also, there are outstandingly suited according to the invention esters of aromatic carboxylic acids having the structural formula

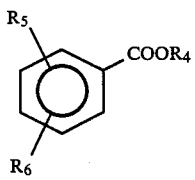

where $R_4$ is the group $CH_3$, $C_2H_5$, n-$C_3H_7$, i-$C_3H_7$, n-$C_4H_9$, i-$C_4H_9$, tert. $C_4H_9$, sec. $C_4H_9$ (i.e., $C_1$ to $C_4$ alkyl), $R_5$ and $R_6$ are substituents which are inert to hydrogen peroxide such as H, halogen, e.g., Cl, F, or Br alkyl such as $R_4$, $CH_3O$, $C_2H_5O$, $COOR_7$ ($R_7$ is as defined as for $R_4$) and $R_5$ and $R_6$ can be in any position in relation to the $COOR_4$ group. Thus, there have proven particularly favorable phthalic acid esters, most preferably diethyl phthalate. Other esters include dimethyl phthalate, dibutyl phthalate, diisobutyl phthalate, di-t-butyl phthalate, diisopropyl phthalate, dipropyl phthalate, dimethyl terephthalate, diethyl terephthalate, diethyl isophthalate, methyl benzoate, ethyl benzoate, diethyl 4-chlorophthalate, diethyl 4-fluorophthalate, dimethyl 4-methyl phthalate, diethyl 4-butyl phthalate, 2-methoxy methyl benzoate, 4-methoxy ethyl benzoate, 2-ethoxy ethyl benzoate, trimethyl trimellitate, triethyl trimellitate.

Furthermore, there can be used carboxylic acid amides or lactams of the general formula

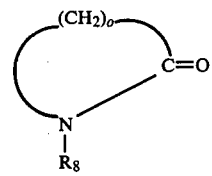

wherein $R_8$ is a straight chain or branched $C_1$-$C_4$ alkyl group, which in a given case can be substituted by halogen, e.g., chlorine, bromine, or fluorine, or a hydroxyl group and o is a number from 2 to 5.

Very good results here have been produced with N-alkyl pyrrolidones having a $C_1$-$C_4$ alkyl group, e.g., N-methyl pyrrolidone, N-ethylpyrrolidone, N-propyl pyrrolidone, N-butyl pyrrolidone, and N-sec. butyl pyrrolidone. Especially preferred is N-methyl pyrrolidone.

Further typical examples of such groups and compounds containing such groups are set forth in German Pat. No. 2038320 on col. 3, line 19 to col. 4, line 12. As stated above, the entire disclosure of German Pat. No. 2038320 is incorporated by reference.

It has also been found that there can be used tetra substituted ureas of the formula

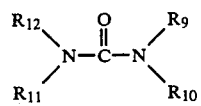

wherein $R_9$, $R_{10}$, $R_{11}$, and $R_{12}$ are $C_1$ to $C_6$ alkyl groups, whereby ureas in which $R_9$, $R_{10}$, $R_{11}$, and $R_{12}$ are the same are preferably used.

Particularly good are tetramethyl urea, tetraethyl urea, and tetrabutyl urea. Other illustrative tetrasubstituted ureas include tetrapropyl urea, tetraisopropyl urea, tetra sec. butyl urea, tetrahexyl urea, dimethyl diethyl urea.

Hydrogen peroxide can be present in the invention in any desired concentrated aqueous solution, best suited are solutions having 3 to 90 weight % hydrogen peroxide, preferably 30–85 weight %.

As stabilizers for the hydrogen peroxide, there can be used any of the customary ones, e.g., as mentioned in Ullmann, Enzyklopadie der technischen Chemie, Vol. 17, 4th edition, page 709.

When employing selenium dioxide as a catalyst in the process of the invention, phenol or substituted phenol or phenol ether is used in excess above the equivalent amount of hydrogen peroxide. There has proven as favorable an excess of 3 to 15 moles based on 1 mole of hydrogen peroxide.

When sulfur dioxide is used as a catalyst, the molar ratio of phenol or the above-mentioned phenol derivatives to 1 mole of hydrogen peroxide is 5 to 20:1, preferably 5 to 15:1, above all 10 moles of phenol or phenol derivative to 1 mole of hydrogen peroxide.

Because of the very small amount of catalyst, there is usually no need to separate off the catalyst. This is a great advantage of the process of the invention.

Furthermore, because of the short reaction time when using sulfur dioxide as the catalyst, the space-time-yield is very favorable. Also, there is avoided the possible danger of decompositions.

When employing selenium dioxide, the ratio of isomers can be controlled in a wide range, indeed in the same system without changes in material, as, e.g., use of a different catalyst or different reaction medium. The ratio of isomers can be changed by the single factor of time.

Unless otherwise indicated, all parts and percentages are by weight.

The process can comprise, consist essentially of, or consist of the stated steps with the recited materials.

The invention is explained in more detail in connection with the following examples.

DETAILED DESCRIPTION

EXAMPLE 1

54.7 grams (0.5 mole) of p-cresol were heated to 94° C. There were added to the stirred melt 0.73 gram of a 1.3 weight % solution of sulfur dioxide in n-propyl acetate and subsequently 7.17 grams of a 23.7 weight % water-free solution of hydrogen peroxide in triethyl phosphate (0.05 mole). The temperature in the reaction solution increased after that to 134° C. After the exotherm died down, there was determined after 10 minutes a hydrogen peroxide reaction of 95.3%. The reaction mixture then contained 3.52 grams (56.7 mmoles) of 4-methylpyrocatechol, and 0.64 grams (10.3 mmoles) of 4-methylresorcinol, which corresponds to a total yield of dihydroxybenzenes of 70.3% based on the hydrogen peroxide reacted.

EXAMPLE 2

94.1 grams (1.0 mole) of phenol were heated to 100° C. There were added to the stirred melt 0.4 grams of a 4.8 weight % solution of sulfur dioxide in isopropyl acetate and subsequently 13.9 grams of a 24.45 weight % water-free solution of hydrogen peroxide in triethyl phosphate (0.1 mole). The temperature in the reaction solution increased after that to 135° C. After the exotherm died down, there was ascertained after twenty minutes a hydrogen peroxide reaction of 91.4%. The reaction mixture then contained 5.20 grams (47.2 mmoles) of pyrocatechol, and 2.54 grams (23.1 mmoles) of hydroquinone, which corresponds to a total yield of dihydroxybenzenes of 76.9%, based on the $H_2O_2$ reacted.

EXAMPLE 3

94.1 grams (1.0 mole) of phenol were heated to 100° C. There were added to the stirred melt 0.4 gram of a 4.85 weight % solution of sulfur dioxide in isopropyl acetate and subsequently 16.04 grams of a 21.19 weight % water-free solution of hydrogen peroxide in diethyl phthalate (0.1 mole). The temperature in the reaction mixture increased to 147° C. After the exotherm died down, after five minutes there was established a hydrogen peroxide reaction of 96.03%. The reaction mixture then contained 2.55 grams (23.2 mmoles) of hydroquinone and 5.54 grams (50.3 mmoles) of pyrocatechol, which corresponds to a total yield of dihydroxybenzenes of 76.5%, based on the hydrogen peroxide reacted.

EXAMPLE 4

75.1 grams (0.5 mole) of 4-tert. butyl phenol were heated to 102° C. There were added to the stirred melt 0.73 gram of a 1.3 weight % solution of sulfur dioxide in isopropyl acetate. There were subsequently added 8.02 grams of a 21.19 weight % water-free solution of hydrogen peroxide (0.05 mole) in diethyl phthalate. The temperature increased to 132° C. After the exotherm died down, there was determined after twenty minutes a hydrogen peroxide reaction of 97.5%. The reaction mixture then contained 7.01 grams (42.2 mmoles) of t-butylpyrocatechol, which corresponds to a yield of 86.6% based on the hydrogen peroxide reacted.

EXAMPLE 5

94.1 grams (1.0 mole) of phenol were heated to 110° C. There were added to the stirred melt 0.033 gram (0.0003 mole) selenium dioxide and 16.04 grams of 21.19 weight % solution of hydrogen peroxide (0.1 mole) in diethyl phthalate. The temperature in the reaction solution increased to a maximum of 154° C. After five minutes, there was determined a hydrogen peroxide reaction of 93.4%. The reaction mixture then contained 6.53 grams (59.3 mmoles) of pyrocatechol and 1.41 grams (12.8 mmoles) of hydroquinone, which corresponds to a total yield of dihydroxybenzenes of 77.2% based on the hydrogen peroxide reacted.

Here after a shorter reaction time there was obtained a higher portion of pyrocatechol to hydroquinone in the ratio 4.63:1.

The entire disclosure of German priority application P.3308726.1 is hereby incorporated by reference.

What is claimed is:

1. A process for the production of a dihydroxy phenol or hydroxyphenyl ether comprising reacting phenol, a substituted phenol, or a phenol ether with hydrogen peroxide in a high boiling organic solvent having not over 1 weight % of water, which organic solvent does not form an azeotrope with water or which forms an azeotrope with water that boils near or above the boiling point of hydrogen peroxide at normal pressure and using a catalyst of the formula $XO_2$ wherein X is sulfur, selenium, or tellurium.

2. A process according to claim 1 wherein the solvent is one which forms an azeotrope with water that boils above the boiling point of hydrogen peroxide.

3. A process according to claim 1 wherein the solvent contains less than 0.5 weight % of water.

4. A process according to claim 1 wherein the catalyst is sulfur dioxide.

5. A process according to claim 4 wherein the sulfur dioxide is employed in gaseous form.

6. A process according to claim 4 wherein the sulfur dioxide is employed dissolved in organic solvent which with boils below the high boiling organic solvent, and which lower boiling organic solvent also forms an azeotrope with water that boils below the azeotrope of the high boiling organic solvent with water.

7. A process according to claim 4 wherein the sulfur dioxide is used in an amount of 0.0001 to 0.1 mole per mole of hydrogen peroxide.

8. A process according to claim 7 wherein the solvent contains less than 0.5 weight % of water.

9. A process according to claim 8 wherein the sulfur dioxide is used in an amount of 0.0005 to 0.01 mole per mole of hydrogen peroxide.

10. A process according to claim 1 wherein the catalyst is selenium dioxide.

11. A process according to claim 10 wherein the selenium dioxide is used in an amount of 0.0001 to 0.5 mole per mole of hydrogen peroxide.

12. A process according to claim 11 wherein the selenium dioxide is used in an amount of 0.0005 to 0.2 mole per mole of hydrogen peroxide.

13. A process according to claim 1 wherein the high boiling organic solvent has the formula

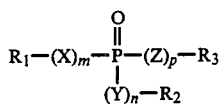

wherein X, Y, and Z are O, a N-($C_1$-$C_8$)-alkyl group or a N-($C_4$-$C_7$)-cycloalkyl group, n, m, and p are each 0 or 1, $R_1$, $R_2$, and $R_3$ are $C_1$-$C_8$ alkyl or $C_4$-$C_6$-cycloalkyl or such an alkyl or cycloalkyl group substituted by halogen, hydroxyl, $C_1$-$C_4$-alkoxy, —CN, or phenyl.

14. A process according to claim 13 wherein the high boiling solvent is a trialkyl phosphate having 1 to 8 carbon atoms in each alkyl group.

15. A process according to claim 14 wherein the phosphate is triethyl phosphate or trioctyl phosphate.

16. A process according to claim 13 wherein the catalyst is sulfur dioxide.

17. A process according to claim 16 wherein the sulfur dioxide is used in an amount of 0.0001 to 0.1 mole per mole of hydrogen peroxide.

18. A process according to claim 13 wherein the catalyst is selenium dioxide.

19. A process according to claim 18 wherein the selenium dioxide is used in an amount of 0.0001 to 0.5 mole per mole of hydrogen peroxide.

20. A process according to claim 1 wherein the high boiling solvent has the formula

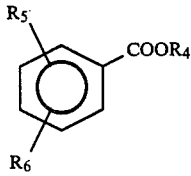

wherein $R_4$ is an alkyl group having 1 to 4 carbon atoms and $R_5$ and $R_6$ are substituents inert to hydrogen peroxide.

21. A process according to claim 20 wherein $R_5$ and $R_6$ are H, Cl, F, alkyl having 1 to 4 carbon atoms, methoxy, ethoxy, or $COOR_7$ where $R_7$ is alkyl having 1 to 4 carbon atoms.

22. A process according to claim 21 wherein the high boiling solvent is an ester of phthalic acid.

23. A process according to claim 22 wherein the high boiling solvent is diethyl phthalate.

24. A process according to claim 20 wherein the catalyst is sulfur dioxide.

25. A process according to claim 24 wherein the sulfur dioxide is used in an amount of 0.0001 to 0.1 mole per mole of hydrogen peroxide.

26. A process according to claim 20 wherein the catalyst is selenium dioxide.

27. A process according to claim 26 wherein the selenium dioxide is used in an amount of 0.0001 to 0.5 mole per mole of hydrogen peroxide.

28. A process according to claim 1 wherein the high boiling solvent has the formula

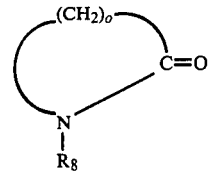

wherein $R_8$ is alkyl of 1 to 4 carbon atoms or such a group substituted by halogen, hydroxy, or a $C_1$ to $C_3$ alkyl group and o is a number from 2 to 5.

29. A process according to claim 28 wherein the high boiling solvent is an N-alkylpyrrolidone having 1 to 4 carbon atoms in the alkyl group.

30. A process according to claim 29 wherein the N-alkylpyrrolidone is N-methylpyrrolidone.

31. A process according to claim 28 wherein the catalyst is sulfur dioxide.

32. A process according to claim 31 wherein the sulfur dioxide is used in an amount of 0.0001 to 0.1 mole per mole of hydrogen peroxide.

33. A process according to claim 28 wherein the catalyst is selenium dioxide.

34. A process according to claim 33 wherein the selenium dioxide is used in an amount of 0.0001 to 0.5 mole per mole of hydrogen peroxide.

35. A process according to claim 1 wherein the high boiling solvent is a tetraalkyl substituted urea of the formula

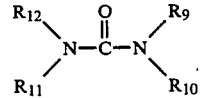

wherein $R_9$, $R_{10}$, $R_{11}$, and $R_{12}$ are alkyl of 1 to 6 carbon atoms.

36. A process according to claim 35 wherein $R_9$, $R_{10}$, $R_{11}$, and $R_{12}$ are the same.

37. A process according to claim 36 wherein the tetraalkyl urea is tetramethyl urea, tetraethyl urea, or tetrabutyl urea.

38. A process according to claim 35 wherein the catalyst is sulfur dioxide.

39. A process according to claim 38 wherein the sulfur dioxide is used in an amount of 0.0001 to 0.1 mole per mole of hydrogen peroxide.

40. A process according to claim 35 wherein the catalyst is selenium dioxide.

41. A process according to claim 40 wherein the selenium dioxide is used in an amount of 0.0001 to 0.5 mole per mole of hydrogen peroxide.

42. A process according to claim 1 wherein there is reacted phenol per se, an alkylphenol, naphthol, hydroxyanthracene, hydroxyphenanthrene, a phenyl alkyl ether, an alkylphenyl alkyl ether, a halophenyl alkylether, hydroxybiphenyl, a halophenol or an alkoxyphenol.

43. A process according to claim 1 wherein the temperature is 40° to 200° C.

* * * * *